(12) United States Patent
Kubota

(10) Patent No.: US 9,068,819 B2
(45) Date of Patent: Jun. 30, 2015

(54) LAYERED OBJECT AND MEASURING APPARATUS AND METHOD

(71) Applicant: CANON KABUSHIKI KAISHA, Tokyo (JP)

(72) Inventor: Oichi Kubota, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 6 days.

(21) Appl. No.: 14/088,201

(22) Filed: Nov. 22, 2013

(65) Prior Publication Data

US 2014/0146306 A1 May 29, 2014

(30) Foreign Application Priority Data

Nov. 26, 2012 (JP) .................................. 2012-257595
Sep. 20, 2013 (JP) .................................. 2013-196074

(51) Int. Cl.
| | |
|---|---|
| G01J 3/00 | (2006.01) |
| G01N 21/35 | (2014.01) |
| G01B 11/06 | (2006.01) |
| G01N 21/3586 | (2014.01) |

(52) U.S. Cl.
CPC ............ G01B 11/06 (2013.01); G01N 21/3586 (2013.01)

(58) Field of Classification Search
USPC ............ 356/51, 630–632, 485, 503; 250/330, 250/338.1, 341.8, 338.4, 341.1, 339.06
See application file for complete search history.

(56) References Cited

U.S. PATENT DOCUMENTS

| | | | |
|---|---|---|---|
| 7,551,269 B2 * | 6/2009 | Itsuji ............................. | 356/51 |
| 7,728,296 B2 * | 6/2010 | Cole et al. ................. | 250/338.1 |
| 7,919,752 B2 * | 4/2011 | Itsuji ........................ | 250/339.06 |
| 8,187,424 B2 * | 5/2012 | Haran et al. .................. | 162/198 |
| 8,440,971 B2 * | 5/2013 | Ouchi et al. ............... | 250/338.1 |
| 8,513,608 B2 * | 8/2013 | Ohtake et al. ............... | 250/341.8 |
| 8,514,403 B2 * | 8/2013 | Ogawa et al. ................ | 356/496 |
| 2008/0137068 A1 * | 6/2008 | Ouchi et al. .................... | 356/51 |
| 2010/0148069 A1 * | 6/2010 | Ouchi ......................... | 250/341.8 |
| 2013/0222788 A1 * | 8/2013 | Kajiki et al. .................... | 356/51 |
| 2013/0235367 A1 * | 9/2013 | Sekiguchi et al. .............. | 356/51 |
| 2013/0334421 A1 * | 12/2013 | Itsuji .......................... | 250/341.8 |
| 2014/0166883 A1 * | 6/2014 | Ono et al. ................ | 250/339.06 |

(Continued)

FOREIGN PATENT DOCUMENTS

| | | |
|---|---|---|
| JP | 10-153547 A | 6/1998 |
| JP | P2004-028618 A | 1/2004 |
| JP | P2005-062188 A | 3/2005 |

(Continued)

*Primary Examiner* — Hoa Pham
(74) *Attorney, Agent, or Firm* — Canon U.S.A., Inc. IP Division

(57) ABSTRACT

A measuring apparatus to identify a material and thickness of each of a plurality of layers included in a layered body, based on a measurement result obtained by measuring a time domain waveform of an electromagnetic wave pulse from the layered body, includes a database configured to store data of a plurality of material candidates and a plurality of thickness candidates, an input unit configured to input a search range of the data stored in the database, and a processing unit configured to reproduce a time domain waveform of an electromagnetic wave pulse from the layered body by employing data of a plurality of material candidates and a plurality of thickness candidates within the search range, and to compare this reproduced time domain waveform and the time domain waveform of the measurement result, thereby identifying the material and thickness of each of the plurality of layers.

14 Claims, 13 Drawing Sheets

(56) References Cited

U.S. PATENT DOCUMENTS

2014/0291524 A1* 10/2014 Kubota et al. .............. 250/341.8
2015/0008324 A1* 1/2015 Itsuji ............................ 250/330

FOREIGN PATENT DOCUMENTS

| JP | P2007-021779 A | 2/2007 |
| JP | P2010-156664 A | 7/2010 |

* cited by examiner

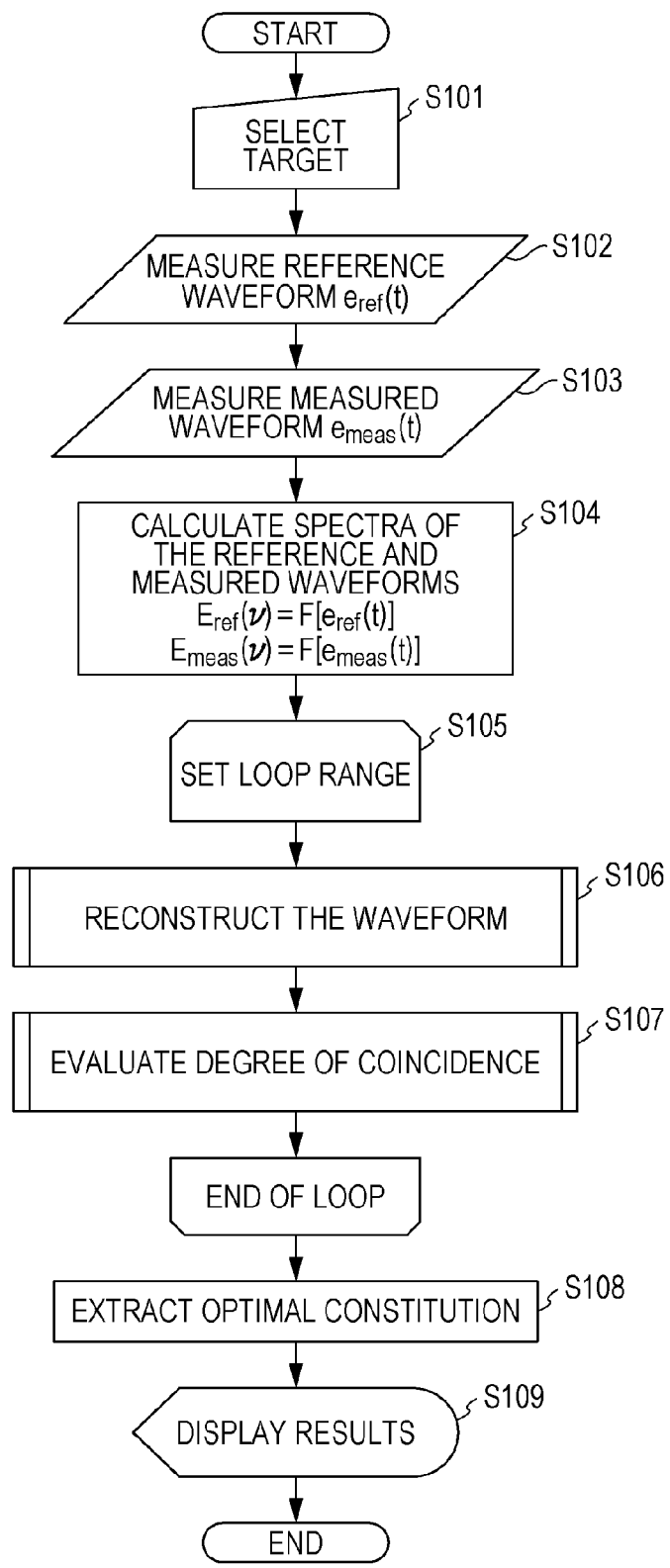

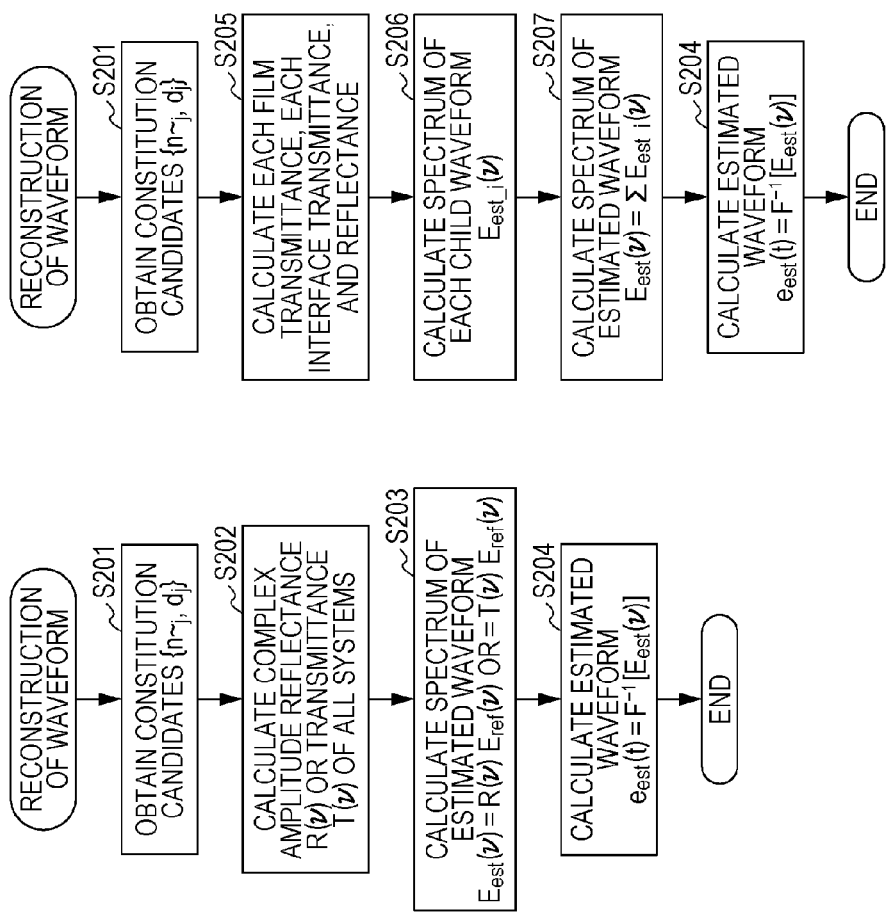

FIG. 7A

| MATERIAL NUMBER | MATERIAL | ATTRIBUTE INFORMATION CLASS: LARGE/MEDIUM/OTHERS | COMPLEX REFRACTIVE INDEX $\tilde{n}(=n-i\cdot\kappa)$ |
|---|---|---|---|
| 1 | MATERIAL 1 | CLASS I/a/1 | $n(\nu), \kappa(\nu)$ OF MATERIAL 1 |
| 2 | MATERIAL 2 | CLASS I/b/1 | $n(\nu), \kappa(\nu)$ OF MATERIAL 2 |
| 3 | MATERIAL 3 | CLASS II/a/2 | $n(\nu), \kappa(\nu)$ OF MATERIAL 3 |
| : | : | : | : |

FIG. 7B

| ID. NUMBER | m | NAME | SAMPLE m |
|---|---|---|---|
| ID. NUMBER | 2 | NAME | SAMPLE 2 |
| ID. NUMBER | 1 | NAME | MULTILAYERED COATING FILM |

| LAYER | MATERIAL RANGE | THICKNESS RANGE |
|---|---|---|
| 1 | 1, 2, ..., 5 | 10 TO 50 (um) |
| 2 | 6, 7, 8 | 100 TO 300 (um) |
| 3 | 1, 2, ..., 10 | 500 TO 1000 (um) |
| : | : | : |

FIG. 8A

| LAYER | ELECTRIC FIELD | | INTERFACE | THICKNESS | MATERIAL |
|---|---|---|---|---|---|
| LAYER m−1 | $E_-$ | $E_+$ | INTERFACE m−1 | | MATERIAL m−1 ($\tilde{n}_{m-1}$) |
| LAYER m | ↑ | ↓ | INTERFACE m | $d_m$ | MATERIAL m ($\tilde{n}_m$) |
| LAYER m+1 | $E'_-$ | $E'_+$ | | | MATERIAL m+1 ($\tilde{n}_{m+1}$) |

FIG. 8B

| LAYER | ELECTRIC FIELD | | INTERFACE | MATERIAL |
|---|---|---|---|---|
| LAYER m | $E_-$ ↑ | $E_+$ ↓ | INTERFACE m | MATERIAL m ($\tilde{n}_m$) |
| LAYER m+1 | ↑ $E'_-$ | ↓ $E'_+$ | | MATERIAL m+1 ($\tilde{n}_{m+1}$) |

LAYERED OBJECT AND MEASURING APPARATUS AND METHOD

BACKGROUND OF THE INVENTION

1. Field of the Invention

The present invention relates to a method for irradiating an electromagnetic pulse on an object, analyzing the obtained electromagnetic pulse to obtain information regarding the object, and a tomography device employing the same.

2. Description of the Related Art

In recent years, there have been developed various inspection techniques employing electromagnetic waves of which the frequency is in a range of 30 GHz to 30 THz, so-called terahertz (THz) waves. Nondestructive inspections taking advantage of transmission properties of terahertz waves are an example. Japanese Laid-Open Patent Publication No. 2004-28618 discloses an example in which a terahertz-band electromagnetic wave pulse is irradiated on a coating film which is a sample, and a reflected electromagnetic wave pulse is detected and analyzed by time-domain spectroscopy (TDS). The film thickness of each coating film formed in multilayers is calculated by checking time difference between peaks of pulses included in the detected signals. Also, directing attention to waveforms of peaks enables the state of each coating film, for example, how dry the film is, to be recognized from changes thereof.

On the other hand, there is also an example of checking the material of a sample from a viewpoint of spectroscopy, employing absorption in a terahertz band of a sample. Japanese Laid-Open Patent Publication No. 10-153547 describes determining a sample by irradiating terahertz-band electromagnetic wave pluses on the sample, and checking the spectrum of transmitted or reflected electromagnetic wave pluses. TDS allows obtaining of location information of each coating film as with the former, or obtaining of the optical property of a sample as with the latter, in order to obtain the amplitude and phase of an electric field at the same time.

However, in the case of the method disclosed in Japanese Laid-Open Patent Publication No. 2004-28618, when the thickness of a layer of a multilayer sample is the same as with the width of an electromagnetic wave pulse within this layer, it is difficult to separate a peak waveform corresponding to each interface of two sides. Also, in the event that a peak waveform derived from multiple reflections within a layer happens to be overlapped with a peak waveform derived from another interface, separation is also difficult in the same way. As a result, there have been cases where identification of the thickness or material of a layer of interest is not performed suitably. On the other hand, with the method disclosed in Japanese Laid-Open Patent Publication No. 10-153547, in the event that a sample has a multilayered structure, it is difficult to individually identify the material of each layer.

Thus, measurement of multilayer samples according to the related art has a problem in that it is difficult to recognize the thickness and material of each layer at the same time.

SUMMARY OF THE INVENTION

According to an aspect of the present invention, a measuring apparatus to identify a material and thickness of each of a plurality of layers included in a layered body, based on a measurement result obtained by measuring a time domain waveform of an electromagnetic wave pulse from the layered body, includes: a database configured to store data of a plurality of material candidates and a plurality of thickness candidates; an input unit configured to input a search range of the data of the plurality of material candidates and the plurality of thickness candidates stored in the database; and a processing unit configured to reproduce a time domain waveform of an electromagnetic wave pulse from the layered body by employing data of a plurality of material candidates and a plurality of thickness candidates within the search range, and to compare this reproduced time domain waveform and the time domain waveform of the measurement result, thereby identifying the material and thickness of each of the plurality of layers.

Further features of the present invention will become apparent from the following description of exemplary embodiments with reference to the attached drawings.

BRIEF DESCRIPTION OF THE DRAWINGS

FIG. 1 is a block diagram illustrating a basic processing procedure in a constitution identifying technique according to an embodiment of the present invention.

FIGS. 2A to 2C are block diagrams illustrating a waveform reconstruction procedure according to an embodiment of the present invention.

FIGS. 7A and 7B are diagrams illustrating a basic configuration of a database.

FIGS. 8A and 8B are diagrams describing a waveform reconstruction technique according to an embodiment of the present invention.

DESCRIPTION OF THE EMBODIMENTS

Figure 3A:
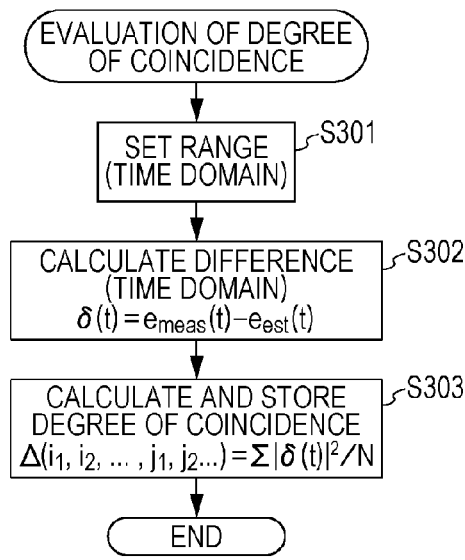
FIGS. 3A and 3B are block diagrams illustrating a procedure for evaluating coincidence of waveforms, according to an embodiment of the present invention.

Hereinafter, an embodiment of the present invention will be described with reference to the drawings.

The present embodiment involves a processing unit irradiating a terahertz-band electromagnetic wave pulse on a layered object (hereinafter, referred to as layered body), to analyze a time domain waveform after transmission or reflection obtained by TDS, and to identify the constitution of a layered body, that is, the material and thickness of each layer. FIG. 1 illustrates a basic processing procedure thereof. A procedure in the event of measuring a portion where the layered body exists will be described here, without discussing each device and data processing technique in detail.

It is a premise that the layered body has a constitution where multiple layers of different materials are stacked, and that there is prepared beforehand a database including data groups of optical properties (frequency dependency of complex refractive index), and representative values and ranges of thickness regarding material candidates making up each layer. The database will be described later. In step S101, a user selects a data group suitable for a layered body to be measured using an input/output device. Subsequent identification of the constitution of the layered body will be made out of these selected data.

In step S102, the processing unit measures a reference waveform $e_{ref}(t)$. Here, the reference waveform is a time domain waveform of an electromagnetic pulse $e_0(t)$ irradiated on the layered body, and includes information of propagation paths (from a generating element to the reference sample, and from the reference sample to a detecting element). Obtaining methods differ depending on the measuring system, and the results measured in a state without a layered body is employed in transmission geometry. On the other hand, results measured by installing a mirror face configured to perform total reflection in the same position as with the sample surface is employed in reflection geometry. In the next step S103, the processing unit sets the layered body to be measured to the measuring system, and measures a measurement waveform $e_{meas}(t)$.

In step S104, the processing unit subjects the previous reference waveform $e_{ref}(t)$ and measured waveform $e_{meas}(t)$ to Fourier transform to obtain the corresponding spectra $E_{ref}(v)$ and $E_{meas}(v)$. Steps S106 to S107 are repetition processes (loops) for analysis. First, in step S105, the processing unit sets a repetition range. This is a range of types of materials and thickness of each layer narrowed down at the time of previously selecting the data group. Next, the processing unit determines parameters of a candidate to be used for analysis with the loop, that is, specific material and thickness values of each layer.

In the next step S106, the processing unit reconstructs a time domain waveform (hereinafter, estimated waveform) $e_{est}(t)$ to be obtained at the time of measuring the layered body using the previously determined parameters and reference waveform $e_{ref}(t)$. In step S107, the processing unit compares the reconstructed estimated waveform $e_{est}(t)$ and the measured waveform $e_{meas}(t)$ obtained by actual measurement. At this time, the processing unit digitizes the degree of coincidence of both waveforms using a suitable evaluation function, and stores this along with a combination of the parameters. A function assuming a value small enough that both agree is selected as the evaluation function, with a range of values being equal to or greater than 0, for example.

In the event that a combination of parameters to be studied remains, the processing unit proceeds to step S106, and upon completion, exits the loop. In step S108, the processing unit extracts a combination of parameters, assuming the minimum value based on the stored value of the evaluation function, reproducing a measured waveform in the most suitable manner. This serves as the result of identifying the material and thickness of each layer. Note that, in the event that this minimum value exceeds a predetermined value that has been set taking the noise level of the measuring system into consideration, the constitution of the sample is regarded as out of the estimated range, and is stored as "unacceptable (not available)".

In the final step S109, the processing unit displays the result. The present procedure is to obtain constitution information of depth direction at a certain point in the layered body, but a two-dimensional or three-dimensional physical property distribution can be obtained by performing the same measurement while changing the irradiation spot. This is visualized as appropriate, whereby a cross-sectional image and a stereoscopic image (tomography image) of the layered body can be obtained.

As described above, it is difficult to directly obtain the constitution of a layered body from the time domain waveform measured therefrom (measured waveform). On the other hand, "reverse" processing represented by the previous step S106, processing to obtain a time domain waveform (estimated waveform) to be measured from the constitution of a known layered body and a reference waveform, is easy. However, in a case of searching for an optimal combination from candidates of the constitutions out of a great number of layered bodies, a considerable amount of computation (duration) is necessary to realize a particular accuracy. Therefore, the search range is narrowed down by aggressively taking advantage of prior knowledge regarding the layered body to be measured. Examples of the prior knowledge include the number of layers of layered bodies, the material of each layer, and representative thicknesses of each layer. Particular accuracy can be improved, and reduction in duration can be anticipated by providing proper initial values, and removing regions not used for searching.

In reality, when the layered body to be measured is decided, a representative layered structure thereof is often within a certain range. For example, in the event that the layered body is a coating film, the materials of the layers are various coating materials. The optical properties of each are measured beforehand, and multiple stored properties are employed. In the same way, values obtained and stored from the same layered body in the past may be employed as the representative values and range of thickness that can be assumed. The previously described database may be large in scale to store materials other than the layered body to be processed, but in step S101, a promising data group (e.g., a data group relating to a multilayered coating film) alone is selected as a candidate, and is taken as a search range.

According to the present embodiment, a suitable data group is selected from the database in which the optical properties of various materials obtained beforehand and thickness of each layer to be taken are stored, and parameters for reproducing measurement results are searched within a range thereof, whereby the thickness and material of each layer of the layered body can be identified at the same time. Computation amount (duration) used for work is suppressed, and high-speed processing can be realized.

First Example

Next, a first example of the present embodiment will be described in detail with reference to the drawings.

After describing a representative apparatus configuration, a model of a layered body to be measured and the database, details of processing such as reconstruction of a waveform and comparison of coincidence will be described.

Figure 4:
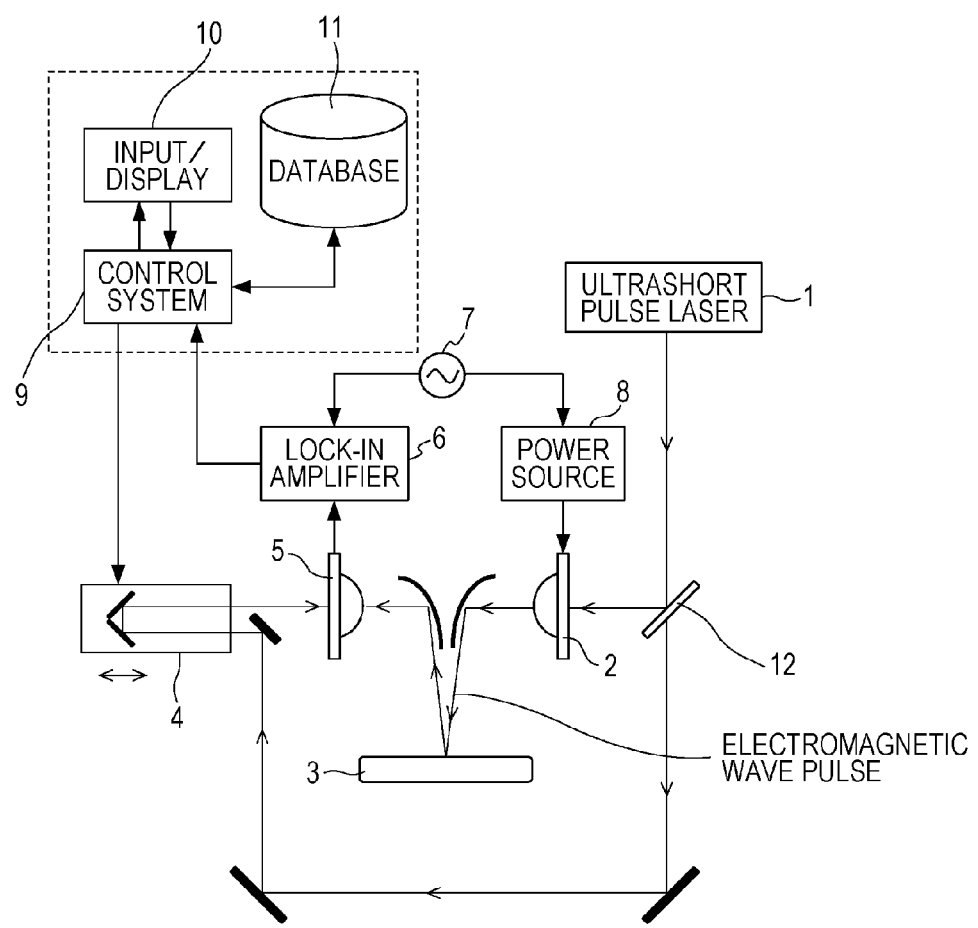
FIG. 4 is a diagram describing an example of a measuring apparatus according to an embodiment of the present invention.

FIG. 4 illustrates an example of the measuring system in the present example. This is a so-called terahertz time domain spectroscopy device in reflection geometry configured to measure electromagnetic wave pulses reflected at a layered body. An ultrashort pulse laser 1 outputs an ultrashort pulse beam in femtosecond order. One of pulse beams branched at a half mirror 12 is irradiated on the rear surface of a photoconductive element 2 to generate a terahertz-band electromagnetic pulse. Intensity thereof is proportional to bias voltage applied from a power source 8.

The terahertz-band pulse extracted from the surface side of the photoconductive element 2 is condensed by a parabolic mirror, and then irradiated on a layered body 3. The parabolic mirror and photoconductive element 2 thereof are equivalent to an irradiation unit. The terahertz-band pulse reflected and returned, having received modulation reflecting the constitution of the layered body, is condensed at the parabolic mirror, and is input to the surface of a photoconductive element 5. The parabolic mirror and photoconductive element 5 thereof are equivalent to a detecting unit. On the other hand, the other half of the ultrashort pulse laser beam branched at the half mirror 12 is input to the rear surface of the photoconductive element 5 via an optical delaying system 4. The photoconductive element 5 outputs current proportional to amplitude intensity of the reflected pules arrived at the surface side while the ultrashort pulse laser beam is input to the rear side.

An oscillator 7 and the power source 8 supply a periodic signal to a lock-in amplifier 6. The amplitude of a reflected terahertz-band pulse is detected with high sensitivity by subjecting a signal detected at the photoconductive element 5 to phase-sensitive detection at the lock-in amplifier 6. A control system 9 controls timing for detecting a reflected terahertz-band pulse arriving at the surface side by controlling the optical delaying system 4 to change the optical path length of the pulse beam input to the rear side of the photoconductive element 5. An output signal is captured from the lock-in amplifier 6 in parallel with sweeping the optical path length, whereby the time domain waveform of a reflected terahertz-band pulse, that is, the measured waveform or reference waveform can be obtained.

Measurement of a reference waveform is preferably performed employing a mirror configured to reflect a light beam in a terahertz band as much as possible, for example, such as a mirror on which a thin gold film is vapor-deposited, or the like. At this time, the positions of the mirror surface and the surface of a sample have to agree accurately, or have to be separated by a predetermined interval. Therefore, experimentally, an arrangement is also made wherein a material (plate material) of which the complex refractive index is known and also the surface is flat is pressed against the sample, and a terahertz-band pulse is irradiated and detected on the sample over the plate material. Reflected light beams from this material and the interface of the sample are preferably employed as reference waveforms. Analysis of the measured waveform is performed while taking into consideration the influence at the time of a terahertz-band pulse passing through this material.

A measurer performs instructions of measurement or display of results such as image forming or the like at a display via an input/output device (input unit) 10 for input or display. On the other hand, the optical properties and dimension information of the material are stored in the database 11 beforehand. When the measurer specifies a data group suitable for a layered body at the input/output device 10, the control system 9 obtains data within this group from the database 11 as appropriate, and uses this for analysis of a measured waveform.

Note that with the present example, the photoconductive element has been employed for generating/detecting a terahertz-band pulse, but another tool having the same advantage may be employed. For example, an ultrashort pulse laser may be irradiated on a material having a nonlinear optical effect (resin such as DAST or the like, or crystal such as LiNbO3 or the like) to take this as a source for generating a terahertz-band pulse. According to this, a pulse light beam with high intensity may be employed as compared to a photoconductive element. At the detection side as well, an arrangement may be made wherein a pulse light beam is irradiated on electro-optical crystal (ZnTe or the like) from the layered body along with probe light, and the intensity is read from change in polarization state. Two-dimensional high-speed imaging may be performed.

Also, the control system 9 including the processing unit, input/output device 10, and database 11 may be configured on a single computer (PC), or may be configured as separate configurations but mutually connected when needed. The computer is caused to execute necessary steps by a program configured to determine the constitution of a layered body. As an example of the latter, the constitution may be conceived wherein the main body of the large-scaled database 11 is disposed remotely from the measuring system. In this case, the control system 9 and database 11 perform exchange of data by communication as appropriate. Further, an arrangement may be made wherein waveform analysis (reconstruction or determination of coincidence) or image processing or the like which relatively requires computing power is performed at a high-speed computer outside the measuring system. With the present embodiment, there are considerable advantages in dividing the tasks into measurement tasks and analysis tasks. Examples of the advantages include that the measuring system can be configured compactly and operating at high speed, that the measurer can select a candidate of a layered body from a detailed and wide-ranging database, and that a computer capable of high-speed and advanced processing is available.

Figure 6A:
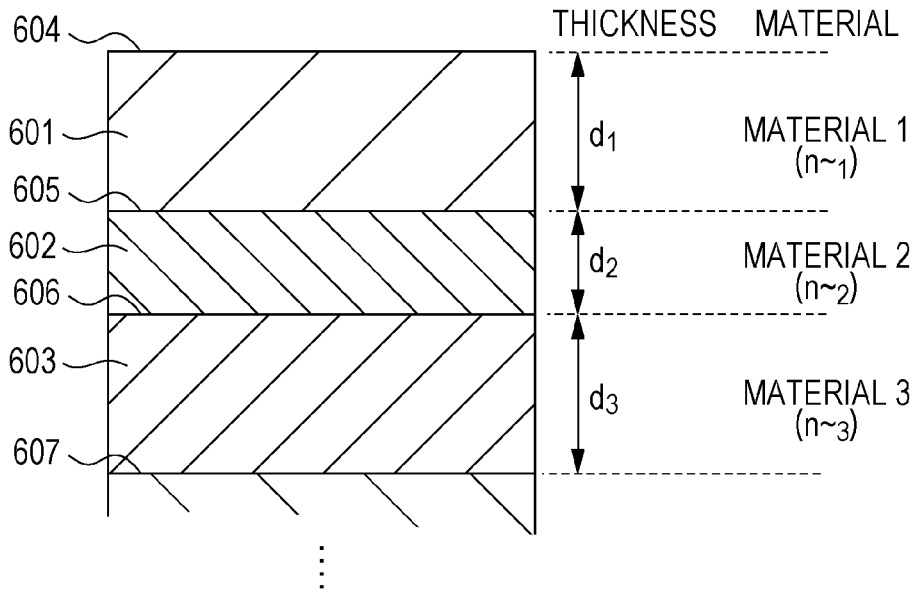
FIGS. 6A to 6C are diagrams describing an example of a constitution of a layered body.
Figure 6B:
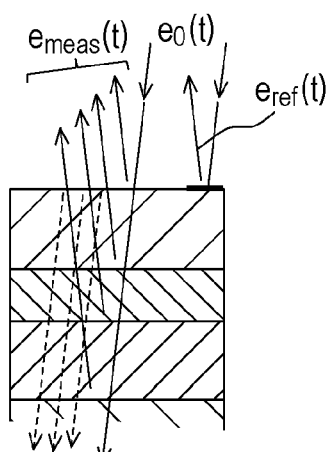
Figure 6C:
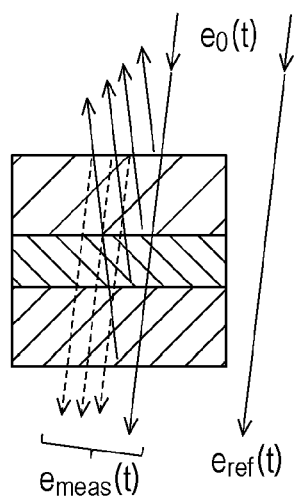

FIGS. 6A to 6C illustrate an example of a layered body to be measured with the present example.

FIG. 6A is a schematic view of a cross-section of a layered body. In order from the surface toward the depth of the layered body, a layer 1 (601), a layer 2 (602), a layer 3 (603), . . . are sequentially stacked. The layers have an optical property according to a material, and complex refractive indexes thereof are sequentially taken as $n\sim_1$, $n\sim_2$, $n\sim_3$, and so on. Interfaces of the layers are sequentially a surface (604), interface 1 (605), interface 2 (606), interface 3 (607), and so on, and thicknesses are as $d_1$, $d_2$, $d_3$, and so on. FIGS. 6B and 6C are cross-sectional schematic views at the time of irradiating a terahertz-band pulse on the layered body. FIG. 6B corresponds to measurement in reflection geometry, and FIG. 6C corresponds to measurement in transmission geometry which will be described later. A pulse (reference waveform) $e_{ref}(t)$ irradiated on the layered body is branched to transmitted light and reflected light each time this arrives at each interface (604 to 607), and receives influence of absorption or dispersion each time this passes through each layer (601 to 603). A measured waveform $e_{meas}(t)$ is overlay of waveforms reflected (b) at the layered body and transmitted (c) from the layered body.

The present embodiment can also be regarded as a technique for assuming that the layered body has a constitution such as FIG. 6A, and identifying the material and thickness of each layer from the reference waveform $e_{ref}(t)$ and measured waveform $e_{meas}(t)$. FIGS. 7A and 7B illustrate a basic configuration of a database to be used for the present embodiment. The present database is configured of two types of datasets of material candidates and thickness candidates in a roughly classified manner.

FIG. 7A is a conceptual diagram of a dataset relating to the optical property of a material candidate. The dataset includes information of (1) a material number specific to a material, (2) the name of the material, and (3) a complex refractive index spectrum of the material, for each material candidate. Enough data to cover at least the materials predicted to make up the layered body is included in the database. As is commonly known, a complex refractive index $n\sim$ can be represented with sum of a refractive index n (real part) and an extinction coefficient κ of an imaginary part.

$$n\sim = n - i \cdot \kappa \quad \text{(Expression 1)}$$

Therefore, (3) may be stored by dividing into a refractive index n and an extinction coefficient κ of an imaginary part. For example, in the event of a multilayered coating film, a complex refractive index in a terahertz band is measured individually regarding coating used for each layer (name: A, B, C, etc.), a spectrum thereof is recorded in the database along with numbers applied as appropriate (1, 2, 3, etc.), and attribute information (large classification, medium classification, etc.). The device to be used for prior measurement of these may be the same device for evaluating a coating film or may be another device. The spectrum measured and obtained in transmission geometry may be used for a measuring device in reflection geometry. However, the band in (3) includes the band of electromagnetic wave pulses that the measuring system generates/detects, and also secures at least width used for reconstruction of a waveform. This is also true regarding resolution. It is important to obtain an accurate spectrum such as sufficiently securing the number of repetitions, or the like.

FIG. 7B is a conceptual diagram of a dataset relating to thickness candidates of a layered body. The dataset includes information of (4) a number specific to a layered body, (5) the name of the layered body, (6) the layer number applied in order from the surface to depth, (7) a material candidate making up this layer (a set of material numbers), and (8) the range of thicknesses that this layer can assume. Enough data to cover a representative range is included in the dataset here as well.

For example, in the event that the measurer has selected "multilayered coating film" as a candidate of a layered body in step S101, material and thickness ranges are determined regarding each layer of the layers 1 to 3 as described above. Various coatings in several drying stages are exemplified as the material of each layer. Hereinafter, analysis of measurement results is advanced within these ranges. Restricting the search range by selection has various advantages. First, the computation amount used for identifying the constitution can be suppressed, and accordingly, the operation of the apparatus increases in speed. Remaining energy may be distributed to improvement in accuracy for calculating the thickness of each layer. Also, removing materials, of which the complex refractive indexes are similar but clearly different and are not used, aids in avoidance of false detection.

Other candidates of layered bodies include a wide range of objects such as paper, plastic, cloth, resins, and so forth. Specifically, in addition to insulating coating films such as booklets, envelopes, packed boxed, cards, electric wires, and so forth, living body tissue is also ones of the objects. In particular, skin and (organ) epithelium tissues have a layered structure, and the thickness and material thereof provide various types of information, including information regarding health. Therefore, for example, spectra are obtained beforehand regarding normal skin tissue and abnormal skin tissue (dry, inflamed, infected with bacteria, cancerous, or the like), and information such as thickness range and so forth is stored in the database along with the name "skin" beforehand. This is also true regarding organs, and spectra thereof are used at the time of clinical analysis of an excised section composition, or observation of the surface layer of tissue using an endoscope or the like.

It is desirable to perform step-by-step and hierarchical classification at the time of storing spectrum information. For example, under a large classification called "skin", there is a medium classification such as "skin cancer", "skin inflammation", and so forth, and there is a small classification such as type, degree of advance, whether benign or malignant, and so forth under "skin cancer". These pieces of information for classifications are numbered and stored as attribute information.

These classifications are effective for improving accuracy and speed of measurement. For example, in the event that skin is taken as an object, first, in step S101, "skin" is selected as a large classification, and measurement is made to recognize overview of an observed portion. Consequently, the thickness range and material candidates and so forth of each layer are recognized, and a search range can be narrowed down. Next, "skin cancer" which is a medium classification is selected, and measurement is made to obtain detailed information regarding the type, degree, and distribution of cancer, which is taken as an aid for diagnosis.

Next, description will be made regarding a procedure for reconstructing the estimated waveform $e_{est}(t)$ from the constitution of an existing layered body and the reference waveform $e_{ref}(t)$, that is, step S106 in FIG. 1. Though several techniques are available, description will be made here regarding a method to reconstruct the estimated waveform $e_{est}(t)$ by obtaining a complex amplitude reflectance of a layered body using a transfer matrix.

FIGS. 2A to 2C illustrate the waveform reconstructing procedure in step S106. Of these, FIG. 2A is a procedure to perform reconstruction using a transfer matrix. Note that FIGS. 2B and 2C are a procedure according to another technique, and accordingly, description will be made within a later-described example. Step S106 is one process within the loop, and is started after the parameters of a layer constitution are determined in step S105. In step S201, in response to this, the complex refractive indexes and thicknesses $\{n\sim_j, d_j\}_i = 1, 2, \ldots$, and so on of the layers used for reconstruction are determined. In step S202, a complex reflectivity spectrum R(ν) of the entire layered body is calculated using the above parameters (details will be described later). In step S203, this is multiplied by the spectrum $E_{ref}(\nu)$ of the reference waveform, thereby obtaining the spectrum $E_{est}(\nu)$ of an estimated waveform. Finally, the spectrum $E_{est}(\nu)$ calculated in step S204 is subject to inverse Fourier transformation to obtain an estimated waveform $e_{est}(t)$.

The complex reflectivity spectrum R(ν) of the entire layered body can be obtained by influence received when passing through each layer, and influence from reflection and transmission at each interface being multiplied. This will be described in order with reference to FIGS. 8A and 8B. For simplification, let us assume that a terahertz-band pulse is perpendicularly input to the layered body.

Frequency ν, point-in-time τ, traveling direction x, progressive waves $E_+(\nu)$ and regressive waves $E_-(\nu)$ of wavenumber k are defined as follows.

$$E_\pm(\nu) = |E_\pm(\nu)| \cdot \exp[i \cdot (2\pi\nu\tau \mp kx)] \quad \text{(Expression 2)}$$

Here, the wavenumber k is obtained as follows when assuming that the complex refractive index is taken as n~.

$$k = n\sim \cdot 2\pi\nu/c \quad \text{(Expression 3)}$$

FIGS. 8A and 8B illustrate the way in which the progressive waves $E_+(\nu)$ and regressive waves $E_-(\nu)$ pass through a layer m with a complex refractive index $n\sim_m$ and thickness $d_m$. In the event of distinguishing by adding a prime' to electromagnetic waves at an interface m, the following relationship holds between the amplitudes of electromagnetic waves at the interfaces m−1 and m. Hereinafter, the transfer matrix regarding the layer m will be represented as $A^{(m)}$.

$$\begin{pmatrix} E_+ \\ E_- \end{pmatrix} = \begin{pmatrix} \exp[ik_m d_m] & 0 \\ 0 & \exp[-ik_m d_m] \end{pmatrix} \begin{pmatrix} E'_- \\ E'_- \end{pmatrix} = A^{(m)} \begin{pmatrix} E'_+ \\ E'_- \end{pmatrix} \quad \text{(Expression 4)}$$

FIG. 8B illustrates the way in which the progressive waves $E_+(\nu)$ and regressive waves $E_-(\nu)$ face each other sandwiching the interface m between the layer m with the complex refractive index $n{\sim}_m$ and the layer m+1 with the complex refractive index $n{\sim}_{m+1}$. In the event of distinguishing by adding a prime' to electromagnetic waves on the layer m+1 side, the following relationship holds between the amplitudes of electromagnetic waves in the layers m and m+1. Hereinafter, the transfer matrix regarding the interface m will be represented as $B^{(m)}$.

$$\begin{pmatrix} E_+ \\ E_- \end{pmatrix} = \quad \text{(Expression 5)}$$

$$\frac{1}{2n{\sim}_m} \begin{pmatrix} n{\sim}_{m+1} + n{\sim}_m & n{\sim}_{m+1} - n{\sim}_m \\ n{\sim}_{m+1} - n{\sim}_m & n{\sim}_{m+1} + n{\sim}_m \end{pmatrix} \begin{pmatrix} E'_+ \\ E'_- \end{pmatrix} = B^{(m)} \begin{pmatrix} E'_+ \\ E'_- \end{pmatrix}$$

A transfer matrix M of the entire layered body from a layer 1 to a layer m with a layer 0 as atmospheric air can be represented with a product of transfer matrixes of the layers and interfaces.

$$M = A^{(0)} B^{(0)} A^{(1)} B^{(1)} \ldots A^{(m)} B^{(m)} = \Pi_{i=0}^{m} A^{(i)} B^{(i)} \quad \text{(Expression 6)}$$

In the event of disposing the layered body in the atmosphere, it is convenient to take the interface 0 (surface) as the origin. At this time, $A^{(0)}$ becomes a unit matrix, and accordingly may be removed from Expression 6. The following expression holds between the progressive waves and regressive waves before and after the layered body. The elements can be calculated by substituting the parameters obtained in step S201 for Expressions 4 and 5, and calculating Expression 6.

$$\begin{pmatrix} E_+ \\ E_- \end{pmatrix} = \begin{pmatrix} M_{11} & M_{12} \\ M_{21} & M_{22} \end{pmatrix} \begin{pmatrix} E'_+ \\ E'_- \end{pmatrix} \quad \text{(Expression 7)}$$

$E'_- = 0$ may be set at the reflection geometry system when no regressive wave enters the final interface due to that the final layer being sufficiently thick or the like. The complex amplitude reflectivity spectrum $R(\nu)$ at this time can be obtained as the next expression.

$$\tilde{R}(\nu) = E_-/E_+ = M_{21}/M_{11} \quad \text{(Expression 8)}$$

On the other hand, in a particular case where a sample is put on the mirror surface (substrate), $E'_+ = E'_-$ holds. The complex amplitude reflectivity spectrum $R(\nu)$ at this time is as follows.

$$\tilde{R}(\nu) = E_-/E_+ = M_{21}/M_{11} \quad \text{(Expression 9)}$$

Finally, description will be made regarding a procedure to evaluate the degree of coincidence between the estimated waveform $e_{est}(t)$ and the measured waveform $e_{meas}(t)$, that is, step S107 in FIG. 1, with reference to FIGS. 3A, 3B, and 9.

Figure 3B:
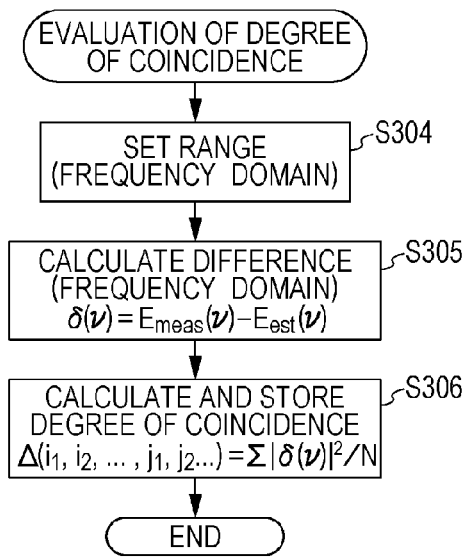

FIG. 3A illustrates a procedure in the event of comparing the estimated waveform $e_{est}(t)$ and measured waveform $e_{meas}(t)$ on the time axis. Note that FIG. 3B will be described within another example.

Figure 9:
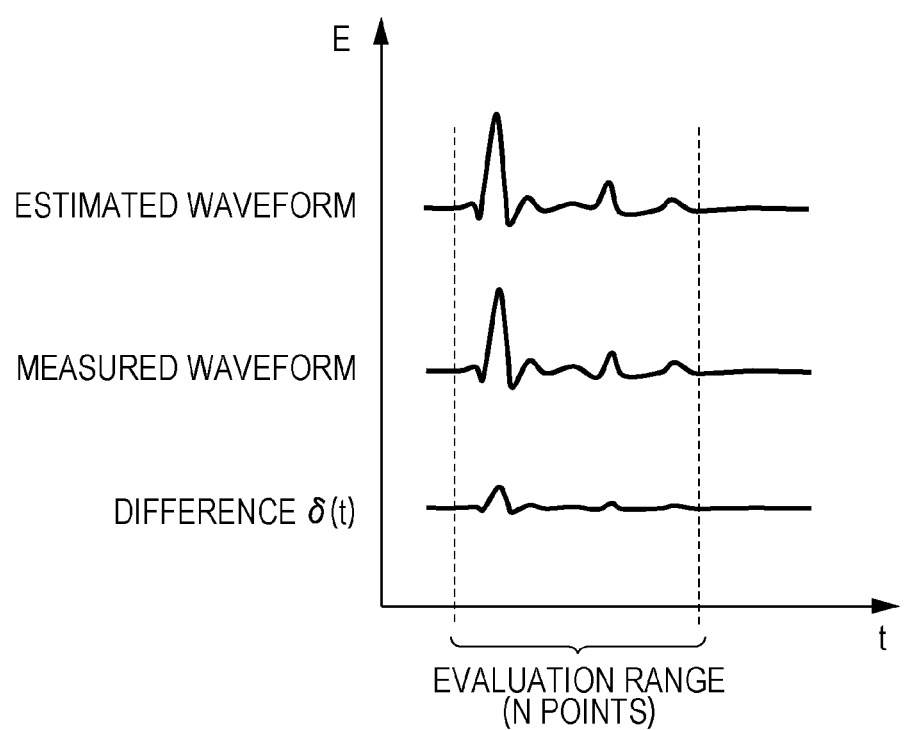
FIG. 9 is a diagram describing a waveform comparison technique on a time axis according to an embodiment of the present invention.

FIG. 9 is a conceptual diagram at the time of actually comparing both waveforms on the time axis. An estimated waveform, a measured waveform, and difference between the estimated waveform and the measured waveform are plotted on the time axis in order from the top. As illustrated in FIG. 9, in general, the waveforms include a region where there is almost no signal. This is primarily to secure a margin on measurement, but in order to accurately perform comparison between the estimated waveform and measured waveform, a margin on measurement does not have to be secured. Therefore, in step S301, the region of interest is narrowed down. Though a specific range may be estimated from the thickness of the layered body, fixing the range to evaluate the degree of coincidence of both waveforms is desirable.

Next, in step S302, the processing unit calculates difference $\delta(t)$ between the measured waveform $e_{meas}(t)$ (t) and the estimated waveform $e_{est}(t)$ on the time axis. Finally, in step S303, the processing unit obtains the degree of coincidence between both pulse waveforms. The processing unit stores the degree of coincidence to an evaluation function $\Delta$ after performing correlation so as to reproduce the material and constitution used for reconstruction later.

$$\Delta(i_1 \cdot i_2 \ldots j_1 \cdot j_2 \ldots) = \Sigma |\delta(t)|^2/N \quad \text{(Expression 10)}$$

Specifically, within the evaluation range set in step S301, the accumulated sum of squares of the difference $\delta(t)$ is divided by the number of measured locations N within the range, and a result thereof is stored in a destination specified with a subscript corresponding to the estimated material and constitution of the layered body. From the definitions, $\Delta$ is constantly positive, and the higher the degree of coincidence between both waveforms, the smaller the value thereof is. Variations other than that in Expression 10 may be conceived for the evaluation function $\Delta$. For example, an arrangement may be made wherein instead of sum of squares of the difference $\delta(t)$, absolute values are accumulated, and a result thereof is divided by the number of measured locations N. Also, in the case of a sample where attenuation of light in a terahertz band is great such as a living body or the like, the closer to the sample surface the layer from which the signal comes is, the greater the intensity thereof. Therefore, the right side in Expression 10 may be calculated after applying a window function which exponentially changes. Now, in order to indicate effectiveness of the above technique, there will be introduced an example wherein an estimated waveform is obtained based on actual measurement results. A terahertz TDS measuring apparatus in reflection geometry was employed as the measuring system, and a layered body made up of three layers was employed as a sample. A constitution thereof is illustrated in Table 1.

TABLE 1

| LAYER | MATERIAL | THICKNESS | (TECHNIQUE) |
|---|---|---|---|
| FIRST LAYER | QUARTZ | 1010 um | (ACTUALLY MEASURED) |
| SECOND LAYER | ATMOSPHERE | 50 um | (THICKNESS OF SHIM) |
| THIRD LAYER | RESIN | 1020 um | (ACTUALLY MEASURED) |

The first layer is a flat quartz plate with thickness of around 1 mm, and the third layer is a resin plate with thickness of around 1 mm which transmits terahertz light well. The second layer is the atmosphere, which was formed by inserting a commercial donut-shaped shim with thickness of 50 um between the above quartz plate and the resin plate as a spacer. At the time of measurement, this sample was held in the atmosphere, and a terahertz-band pulse was irradiated toward a central gap portion from the quartz plate side.

Figure 10:
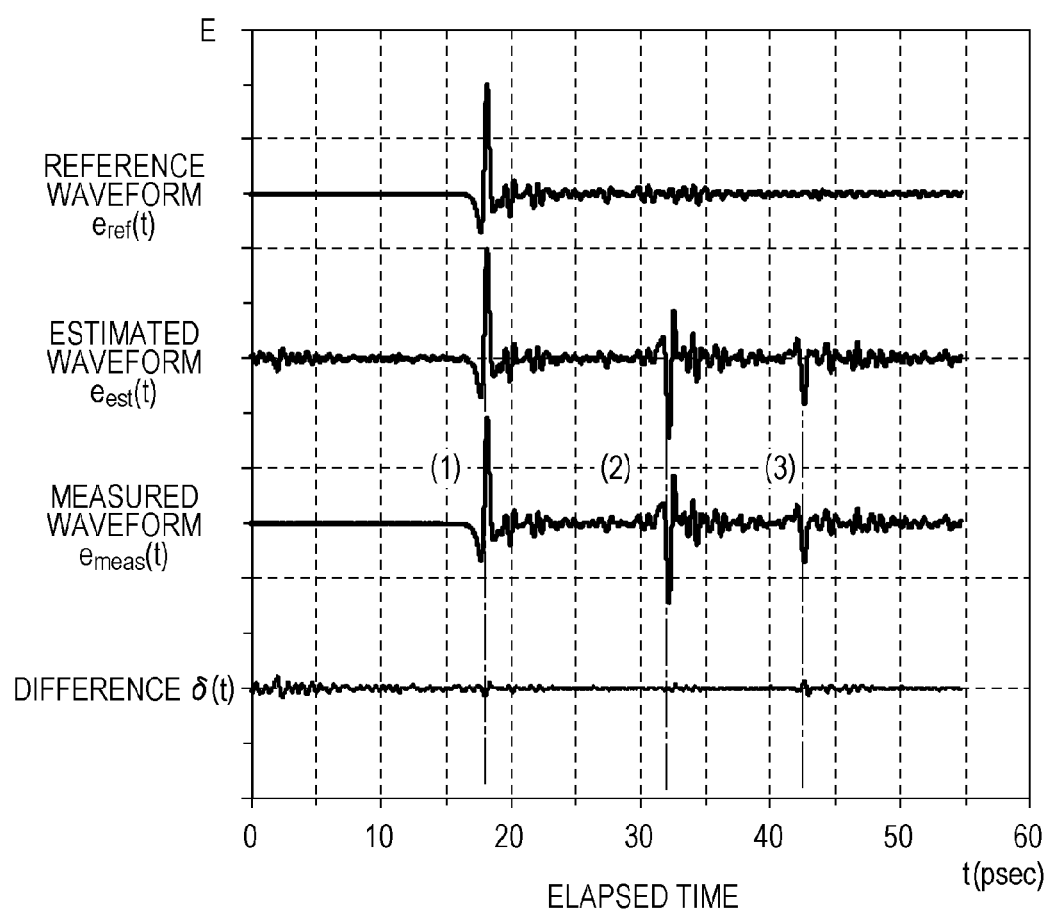
FIG. 10 is a diagram comparing an actually measured waveform and a calculated waveform.

FIG. 10 illustrates measurement results and an estimated waveform obtained by the present technique. The horizontal axis is time, and the vertical axis is amplitude, and each time domain waveform is disposed so as to avoid overlapping. The reference waveform $e_{ref}(t)$, estimated waveform $e_{est}(t)$, measured waveform $e_{meas}(t)$, and difference $\delta(t)$ between the estimated waveform and measured waveform are illustrated in order from the top. With regard to the reference waveform $e_{ref}(t)$, a result obtained by measuring an Au mirror (disposed so that the surface position is common to that of the sample) was employed.

Here, the reference waveform in the top tier is standardized with the own maximum value, waveforms at the second tier and thereafter, measured waveform, and difference $\delta(t)$ are each standardized with the maximum value of the estimated waveform. It is recognizable at a glance that the estimated waveform almost reproduces the measured waveform, and difference between both almost approximates 0. At the time of identifying a constitution, there were employed six types of data groups in total obtained by selecting three types of quartz and two types of resins from data of complex refractive indexes of various materials obtained with prior measurements and by adding the atmosphere (n=1, k=0) thereto. Also, the thickness range of each layer was determined with reference to the actual measured values.

The constitution of the sample identified from a waveform most suitably reproducing the measured waveform is illustrated in Table 2.

TABLE 2

| LAYER | MATERIAL | THICKNESS | (SEARCH RANGE) |
|---|---|---|---|
| FIRST LAYER | QUARTZ | 992 um | (980 to 1020 um) |
| SECOND LAYER | ATMOSPHERE | 64 um | (40 to 80 um) |
| THIRD LAYER | RESIN | 998 um | (980 to 1020 um) |

It can be seen that the material of each layer is correctly identified, and thickness thereof has a closer value, as compared to Table 1.

When interpreting FIG. 10, Peak (1) is the sample surface, and Peak (3) is the maximum reflection from the rear surface. On the other hand, in Peak (2), reflections from both interfaces between the quartz and the atmosphere and between the atmosphere and the resin are overlapped. It is difficult to understand such a situation just by visually inspecting. The material and thickness of each layer of the sample can be recognized at the same time by employing the present technique.

Description has been made so far regarding reconstruction of an estimated waveform, and a method for evaluating the degree of coincidence with a measured waveform. In order to perform such comparison, time scales (the number of data points, and a time interval) of the estimated waveform and measured waveform have to agree. In order thereto, it is desirable that the frequency scale of the complex refractivity spectrum $\tilde{n}(\nu)$ stored in the database 11, and the frequency scale of the spectrum $E_{ref}(\nu)$ of the reference waveform agree. If performing measurement with the same condition each time, it would be sufficient to prepare a complex refractivity spectrum of a material with a frequency scale in accordance with the time scale thereof, and store this in the database 11. However, in general, conditions such as the number of measured points and time interval change, and accordingly, there has to be performed interpolation, approximation, or thinning of data has to be performed as appropriate at a calculation process.

Therefore, for example, in step S203, conversion of the scale is performed. The spectra of the measured waveform measured with the same time scale and reference waveform are taken as $E_{meas}(\nu)$ and $E_{ref}(\nu)$ (steps S102 to S104). The complex amplitude reflectance $R(\nu)$ regarding all of the systems is calculated using the complex reflectivity spectrum $\tilde{n}(\nu)$ stored in the database (steps S201 to S202). Next, interpolation or approximation is performed so that the frequency scale of the complex amplitude reflectance $R(\nu)$ agrees with that of the reference waveform spectrum $E_{ref}(\nu)$. The reference waveform spectrum $E_{ref}(\nu)$ is multiplied by the reflectance $R_{mod}(\nu)$ after adjustment to obtain an estimated waveform spectrum $E_{est}(\nu)$ (step S203). Subsequent processing is the same as described above.

A simple table format has been assumed so far regarding the data of complex refractivity spectra stored in the database 11 (hereinafter, spectrum data). However, it is not desirable in respects of storage capacity, calculation speed, costs, and so forth for the apparatus which actually uses the data to store raw spectrum data with high precision regarding a large number of materials. Therefore, an arrangement may be made wherein data of a complex reflectance of each type of material is compressed by wavelet or the like and then stored in the database 11. In step S101, after selecting a data group from the database, each compressed data is decompressed, and is employed as spectrum data for waveform reconstruction. Alternatively, in step S201, spectrum data to be used is decompressed each time the data is needed for waveform reconstruction. Simultaneous with decompression, scale conversion to have the time scale agree with the measured waveform may be implemented. At this time, time scale matching in step S203 may be omitted.

Also, the database 11 and control system 9 may physically be separated. For example, a great number of spectrum data with high precision and a broad bandwidth are stored in the database 11 beforehand. Upon the measurer specifying an object at the input/output device 10 in step S101, the control system 9 requests the database 11 for a data group to be used via a suitable network. The database 11 converts the spectrum data (group) to be used as appropriate so as to have the requested time scale and band, and sends back to the control system 9. With another example, the database 11 can be added to and changed. The measurer externally obtains spectrum data with precision and band being adjusted via a communication or storage medium according to his/her purpose, and updates the database 11.

Also, description has been made so far so that each layer of the layered body has a uniform composition for simplification of description. However, scattering of terahertz light in a certain layer, and scattering due to surface (interface) roughness can also be included in the present technique by approximation as to a transfer matrix.

Second Example

Figure 5:
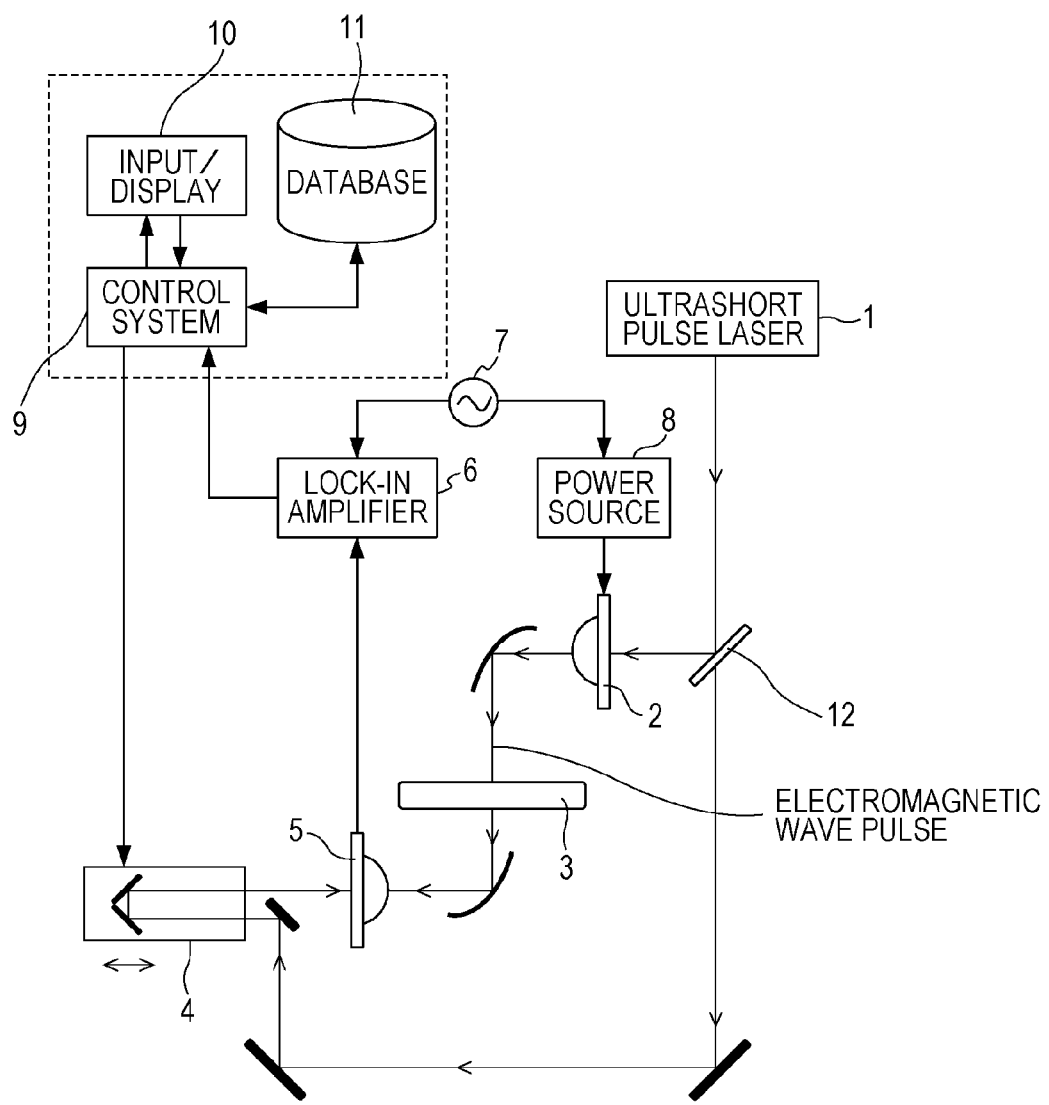
FIG. 5 is a diagram describing another example of a measuring apparatus according to an embodiment of the present invention.

A second example of the present embodiment will be described with reference to FIG. 5. The previous example has been the terahertz time domain spectroscopy measuring apparatus in reflection geometry, but the present example is a case in transmission geometry. The peripheral layout of the layered body 3 differs in comparison with the previous example (FIG. 4). Hereinafter, description of common portions will be omitted as much as possible, and description will be made focusing on difference in constitutions and operation.

With the present example, a terahertz-band pulse extracted from the surface side of the photoconductive element 2 is condensed, and then irradiated on the layered body 3. The pulse which has transmitted through the layered body 3 is condensed again, and is input to the surface of the photoconductive element 5. Obtaining of a time domain waveform is performed in the same way as with the previous example, but the present example differs from the previous reflection geometry system in the method for obtaining the reference waveform $e_{ref}(t)$. That is to say, a result measured in an empty state in which the layered body 3 has been removed from the apparatus is employed as the reference waveform $e_{ref}(t)$.

Also, there is also difference in step S106 wherein the estimated waveform $e_{est}(t)$ is reconstructed. With the previous example, the complex amplitude refractivity spectrum $R(v)$ of the entire layered body has been obtained in step S202, but with the present example, a transmittance spectrum $T(v)$ is obtained. Thereafter, in step S203, the spectrum $E_{ref}(v)$ of the reference waveform is multiplied by the transmittance spectrum $T(v)$, and in step S204, which is subjected to inverse Fourier transformation, thereby finally obtaining an estimated waveform $e_{est}(t)$.

The transmittance spectrum $T(v)$ of the entire layered body may be obtained using a transfer matrix in the same way as with the complex amplitude refractivity spectrum $R(v)$. Specifically, there may be obtained a ratio of electric field strength in the event of having a layered body and electric field strength in the event of having no layered body, at the position of the final layer interface of the layered body. The following expression is obtained from electric field strength (Expression 7) before and after the layered body and phase change in the atmosphere assuming that no regressive wave is input to the interface of the final layer.

$$\tilde{T}(v) = \frac{E'_-}{E_- \cdot \exp\left[-ik_1 \sum_{l=1}^{m} d_l\right]} = \left(M_{11} \cdot \exp\left[-i\frac{2\pi v}{c}\sum_{l=1}^{m} d_l\right]\right)^{-1} \quad \text{(Expression 11)}$$

Subsequent steps (S107 and so on) are the same as with the first example, and accordingly will be omitted.

According to the present example, analysis employing the present technique can be performed for measurement in transmission geometry as well. The transmission geometry system is more suitable than the reflection geometry system depending on the layered bodies to be processed. Complementary information may be extracted from measurement results obtained in both displacements, and effectiveness of the present example is improved.

Third Example

With the previous first and second examples, a calculation technique employing a transfer matrix has been used in the waveform reconstruction in step S107. With the present example, description will be made regarding a case employing another waveform construction technique.

Pulse light within the layered body is branched while reducing the amplitude each time the pulse light arrives at an interface (FIGS. 6B and 6C). With the present example, the pulses are individually calculated and summed, thereby reconstructing the waveform. FIG. 2B illustrates the procedure thereof.

In step S201, the values of the complex reflectance and thickness of each layer (within a certain loop condition) are determined. Next, in step S205, the processing unit calculates the phase term at the time of traversing each layer (influence of absorption or dispersion), and the complex amplitude transmittance or transmittance of each interface. The former is obtained by Expression 4 in the displacement in FIG. 8A, and the latter is obtained by the following expression in the displacement in FIG. 8B.

$$t_{m,m+1} = E_+'/E_+ = 2n\sim_m/(n\sim_{m+1} + n\sim_m) \quad \text{(Expression 12)}$$

$$r_{m,m+1} = E_-/E_+ = (n\sim_{m+1} - n\sim_m)/(n\sim_{m+1} + n\sim_m) \quad \text{(Expression 13)}$$

The amplitude intensity of a certain pulse can be calculated once the path thereof is determined. For example, amplitude $E_-$ in the event that the reference waveform $e_{meas}(t)$ of amplitude $E_{0+}$ is reflected at an interface with the layer 3, goes to and from the layer 2, and returns to the atmosphere again, is as follows.

$$E_- = t_{1,2} r_{2,3} t_{2,1} \exp[-2ik_2 d_2] \cdot E_{0+} \quad \text{(Expression 14)}$$

Waveforms which should have been reflected at or should have transmitted through such a layered body (hereinafter, child waveforms) can infinitely be conceived. Therefore, in step S206, the processing unit checks amplitude simultaneously while obtaining these child waveforms $E_{est\_i}(v)(i=1, 2, \ldots,$ and so on) and in the event that the maximum value thereof is equal to or smaller than a predetermined threshold value ($E_{EL+} \times 10^4$ or the like), quits subsequent calculation. In step S207, the processing unit adds all of effective child waveforms, and calculates an estimated waveform spectrum $E_{est}(v)$. Finally, in step S204, the processing unit subjects this to inverse Fourier transformation to obtain an estimated waveform $e_{est}(t)$.

The amplitude of a child waveform rapidly decreases with a layered body having great attenuation such as a living body, and accordingly, there are few effective child waveforms themselves. In such a case, it is convenient from an aspect for suppressing computation amount to employ the present example. Also, in the event of introducing slight shift from an ideal such as influence of scattering derived from roughness of an interface, the present example is also easier.

Also, as another waveform reconstructing technique, a time domain waveform reflected or transmitted may directly be calculated using an existing electromagnetic field analyzing technique such as FDTD. FIG. 2C illustrates the procedure thereof.

In step S201, the values of the complex reflectance and thickness of each layer (within a certain loop condition) are determined. In step S208, the processing unit divides a region where calculation is performed into meshes with reference to the value of thickness of each layer. In step S209, the processing unit determines the physical property value (complex refractive index) of a medium in a region where calculation is performed, and determines a boundary condition. In step S210, the processing unit performs electromagnetic field analysis, and in step S211 finally obtains an estimated waveform $e_{est}(t)$.

An advantage of the technique for calculating estimated waveforms using electromagnetic analysis is in that various distributions can flexibly be handled such as a case where the physical property value of a medium gradually changes, or the like. Also, the time domain waveform is directly calculated, and accordingly, the spectra of reference and measured waveforms do not have to be calculated (step S104).

Fourth Example

A fourth example of the present embodiment will be described with reference to the drawings. With the previous examples, description has been made in step S301 assuming that a region where measured and estimated time domain waveforms are compared (evaluation range) is fixed. The present example takes the reflection geometry as fundamental, and moves the evaluation range.

The present example directly measures a time domain waveform from each layer interface using time-resolved spectroscopy. Accordingly, each time domain waveform includes information originating closer to the surface of the layered body the earlier the region. Therefore, the constitution of the sample is estimated in order from the side closer to the surface, and moving or expanding the evaluation range over time.

Figure 12:
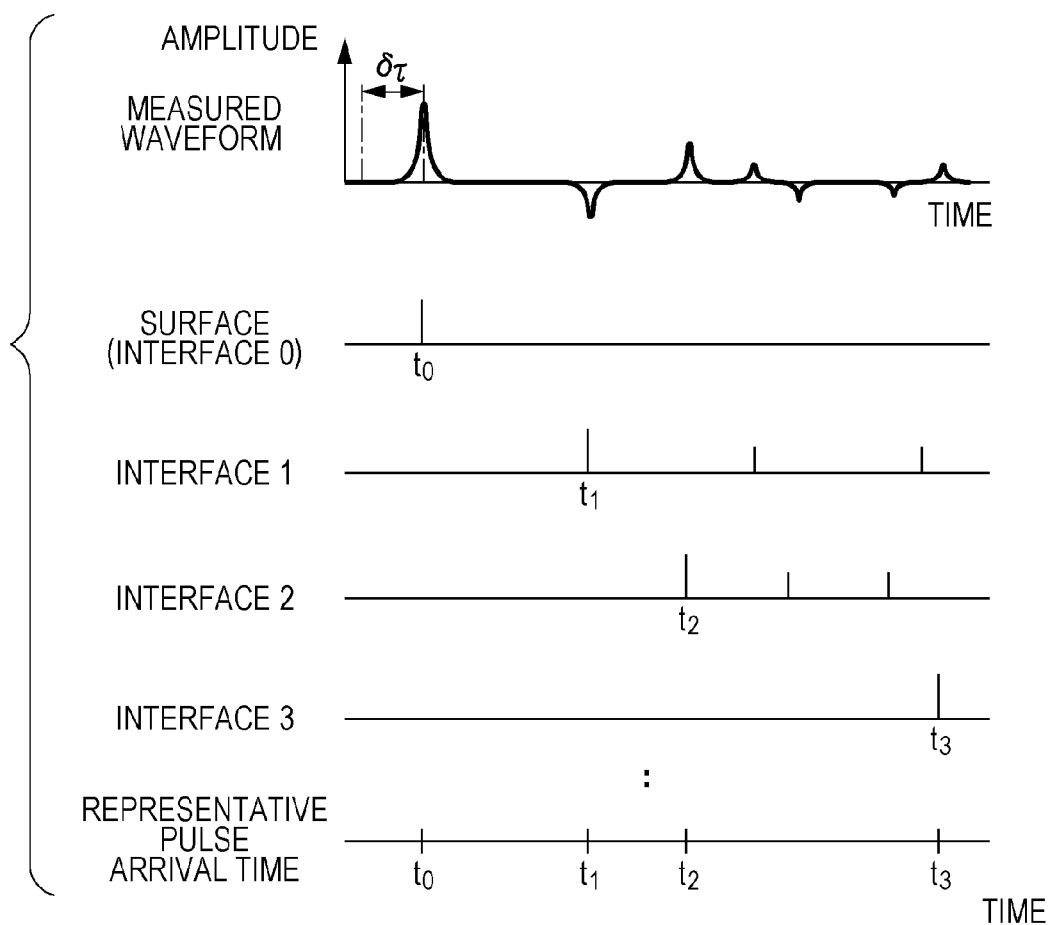
FIG. 12 is a diagram describing an arrival point-in-time of a principal pulse waveform.

FIG. 12 illustrates a representative arrival point-in-time of a pulse reflected from each interface. As an example, there is estimated reflected light in the event of irradiating a terahertz-band pulse on the sample in FIG. 6A. A measured waveform on the top tier is superposition of pulses reflected from the interfaces. Also, the next tier and thereafter estimate the arrival point-in-time of a representative pulse thereof and illustrate this according to interfaces, the earliest detection points-in-time thereof are taken as $t_0$, $t_1$, $t_2$, and $t_3$, respectively. Note that the value of point-in-time $t_m$ is provided as follows with the point-in-time $t_0$ when a pulse was detected from the surface as a reference ($t_0=0$).

$$t_m = \sum_{k=1}^{m} \frac{2n_k d_k}{c} \quad \text{(Expression 15)}$$

In general, time domain waveforms detected at detection point-in-time $t_m$ and theretofore include only information up to the layer m. Therefore, the present example advances estimation of constitutions in order from the surface to the depth such as estimating the constitution of the layer 1 with time domain waveforms from beginning to point-in-time $t_1$, then estimating the constitution of the layer 2 up to point-in-time $t_2$.

The actual procedures are as follows.

(1) A margin $\delta_t$ and a predetermined time interval $\Delta\tau_0$ are determined.

(2) One set of constitution candidates is selected from the selected data group, and representative pulse arrival point-in-time ($t_1$, $t_2$, . . . ) in the constitutions thereof are obtained.

(3) An evaluation range is set with the surface as a target and waveforms are compared. The position of the surface and the material of the first layer (layer 1) are estimated by repeating selecting and comparing candidates.

(4) An evaluation range is set with the interface 1 as a target and waveforms are compared. Similarly, the position of the interface 1 and the material of the second layer are estimated.

(5) Similarly, an evaluation range is set and waveforms are compared while sequentially changing an interface serving as a target toward the depth. In the event that an interface k is taken as the target, a position thereof and the material of the k+1'th layer are estimated.

(6) Upon estimation in the final layer being completed, the procedure ends.

Here, the margin $\delta_t$ is a margin at the time of evaluating a time domain waveform, and is determined beforehand according to a measuring system to be used. The actual terahertz-band pulse has, as viewed with the measured waveform in FIG. 10, a range before and after a peak point-in-time of a waveform. Therefore, the margin $\delta_t$ is introduced to calculate a true start point-in-time of the pulse via a more understandable peak point-in-time. For example, in order to evaluate the time domain waveform in FIG. 10 including the base, a suitable $\delta_t$ is around 4 ps.

On the other hand, the predetermined time interval $\Delta\tau_0$ determines suitable width of an evaluation range. In order to perform comparison between both of a measured time domain waveform and an estimated time domain waveform in a high-precision manner, the neighborhood of an interface of interest may be evaluated after securing an interval sufficient for detecting shift of a peak. Such suitable width depends on the measuring system, and width of a terahertz-band pulse to be irradiated becomes a guide thereof. In light of demand that shift of a peak on the time axis be detected regardless of before or after the peak, triple or more the full width at half maximum (FWHM) W of the pulse, preferably around 30 times the width, is employed as the predetermined time interval $\Delta\tau_0$. Accordingly, $\Delta\tau_0$ satisfies $3W \leq \Delta\tau_0 < t_m$. For example, with the example in FIG. 10, the FWHM of a terahertz-band pulse is approximate 0.3 ps. Therefore, at least $\Delta\tau_0=1$ ps, preferably width of around 10 ps is secured for evaluation.

Setting of evaluation ranges is an important portion in the present example, and accordingly described in detail with reference to FIGS. 13A to 13D.

Figure 13A:
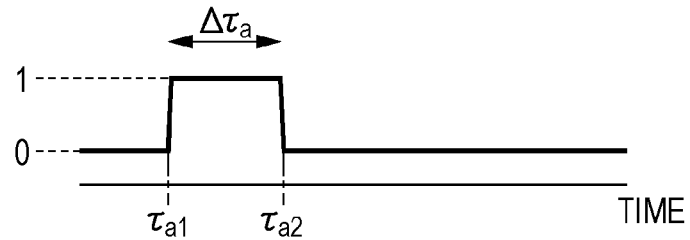
FIGS. 13A to 13D are diagrams describing another waveform comparison technique on a time axis according to an embodiment of the present invention.

FIG. 13A is an example of a basic window function for waveform comparison. A desired evaluation range is clipped by multiplying a time domain waveform by a window function which has a value of 1 or 0, and changes in a step manner along the time axis. Clipping start and end point-in-time and width ($\tau_{a1}$, $\tau_{a2}$, $\Delta\tau_a=\tau_{a2}-\tau_{a1}$) are determined as follows depending on cases.

Figure 13B:
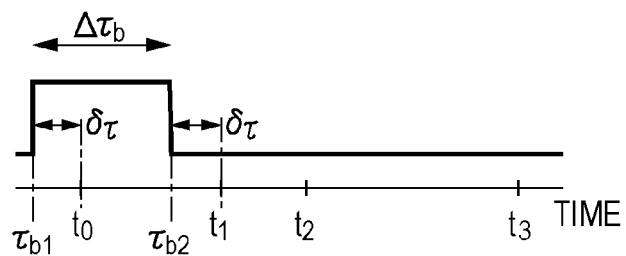

FIG. 13B illustrates the way in which evaluation in the procedure (3) is performed after ending the previous procedures (1) and (2).

First, a margin is estimated by $\delta\tau$ from pulse arrival point-in-time $t_0$ from the surface, and start point-in-time $\tau_{b1}$ in the evaluation range is determined ($\tau_{b1}=t_0-\delta\tau$). Next, similarly, a margin is estimated by $\delta\tau$ from representative pulse arrival point-in-time $t_1$ from the interface 1, and end point-in-time $\tau_{b2}$ in the evaluation range is obtained ($\tau_{b2}=t_1-\delta\tau$).

When confirming that width $\Delta\tau_b=\tau_{b2}-\tau_{b1}$ is wider than a predetermined time interval $\Delta\tau_0$ ($\Delta\tau_b \geq \Delta\tau_0$), this range is taken as the evaluation range for waveform comparison. The position $t_0$ of the surface converted into arrival point-in-time, and the material $n\sim_1$ (complex refractive index) of the first layer, are identified as a result of evaluation. Parameters other than these are irrelevant to the evaluation on the present stage, and accordingly, appropriate initial values are substituted for such parameters. Next, the setting of evaluation ranges proceeds to estimation of the position of the interface 1 and the material of the second layer.

Figure 13C:
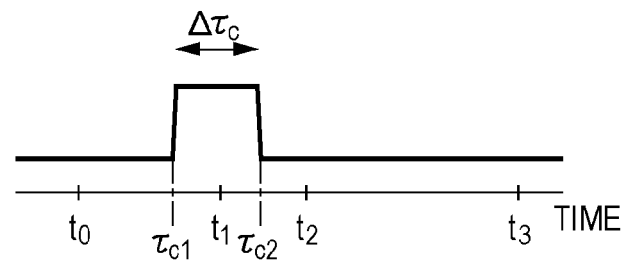

FIG. 13C illustrates a certain stage in the procedure (4). Margins $\Delta\tau$ are estimated from the representative pulse arrival points-in-time $t_1$ and $t_2$ from the interfaces 1 and 2 respectively, and start point-in-time $\tau_{c1}$ and end point-in-time $\tau_{c2}$ of the evaluation range are obtained. Width thereof is $\Delta\tau_c=\tau_{c2}-\tau_{c1}$. At this time, in the event that a layer to be processed (here, first layer) is thin, the width $\Delta\tau_d$ may be narrower than the predetermined time interval $\Delta\tau_0$ ($\Delta\tau_d < \Delta\tau_0$). In this case, pulse separation fails, and evaluation is not performed with sufficient precision. Accordingly, let us consider that the evaluation range is extended in the direction away from the surface, by one more layer.

Figure 13D:
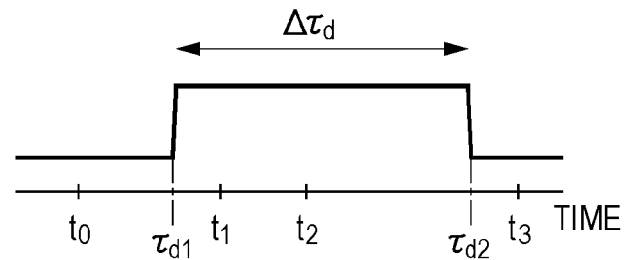

FIG. 13D illustrates another stage in the procedure (4) wherein the evaluation range has been extended. A margin $\Delta\tau$ is estimated from representative pulse arrival point-in-time $t_3$ from the interface 3, and end point-in-time $\tau_{c2}$ of the evaluation range is obtained. Point-in-time $\tau_{d1}$ is the same as the last time ($\tau_{d1}=\tau_{c1}$), and width becomes $\tau_d=\tau_{d2}-\tau_{d1}$. When confirming that the width thereof is wider than the predetermined time interval $\Delta\tau_0$ ($\Delta\tau_d \geq \Delta\tau_0$), this range is employed as the evaluation range. Conversely, in the event of narrower than the predetermined time interval $\Delta\tau_0$ ($\Delta\tau_d < \Delta\tau_0$), the range is further extended in the same procedure. The evaluation range thus employed includes multiple interfaces and layers, and accordingly, these are estimated together at the time of evaluation. In the event of the present example, the positions $t_1$ and $t_2$ of the interfaces 1 and 2, and the materials n~$_2$ and n~$_3$ of the second and third layers are estimated together. The positions of the layer 3 and thereafter and the materials of the fourth layer and thereafter are irrelevant to the evaluation, and accordingly may be excluded from estimation targets.

As with the present example, a technique to estimate the constitution of each layer of a layered body while moving the evaluation range in the order of elapsed time allows estimation to be ended in a shorter period of time as compared to a normal technique. The greater the number of layers, the more complicated the constitution is, and the greater this advantage is. With a normal technique, parameters such as the thickness and material of each layer are exponentially changed within the selected range. Therefore, combinations of parameters to be studied exponentially increase as the number of layers increases. On the other hand, with the technique of the present example, the number of parameters to be estimated at once is suppressed to several types. Accordingly, even if a range assigning process is additionally included, increase in computation along with increase in total number is suppressed to linear increase. For example, let us consider a situation wherein, with regard to a layered body of five layers in total, the parameters (refractive index n, extinction coefficient κ, and thickness d) are each estimated from ten candidates. With a normal technique, the optimal constitution has to be estimated by evaluating $(10^3)^5=10^{15}$ parameters together, but on the other hand, with the present technique, only $10^3$ parameters at most have to be evaluated five times, so calculation amount can be suppressed.

Fifth Example

A fifth example of the present embodiment will be described with reference to the drawings. With the examples described above, the degree of coincidence between the measured waveform $e_{meas}(t)$ and the estimated waveform $e_{est}(t)$ has been evaluated only on the time axis. A peak position in a time domain waveform greatly depends on total optical path length over which a pulse has passed. That is to say, we can say that this is a technique focusing on evaluating coincidence on the time axis, regarding the refractive index difference of a real part of complex refractive index of the layered body.

On the other hand, when looking at the complex refractive spectrum of each material in a terahertz band, features frequently appear in an absorption coefficient (extinction coefficient) as compared to a refractive index. In the event of a material having a characteristic spectrum (so-called fingerprint spectrum) in a terahertz band, it is effective to perform identification thereof using an absorption coefficient (extinction coefficient).

Figure 11:
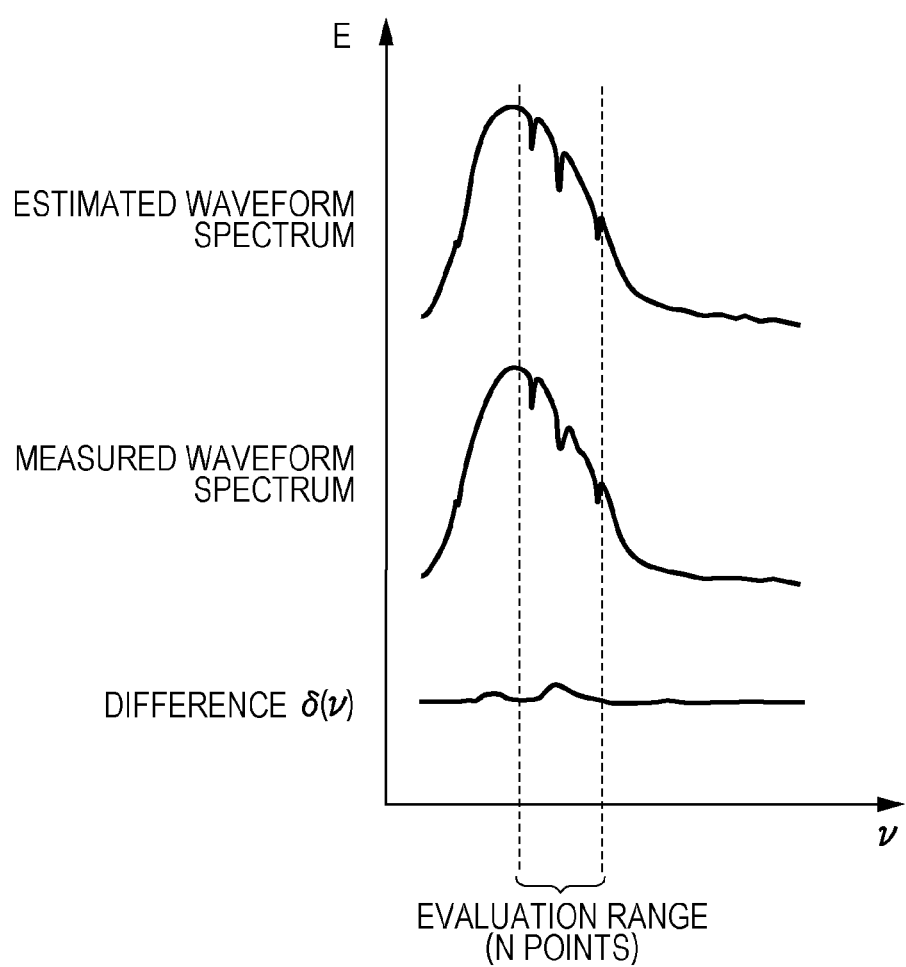
FIG. 11 is a diagram describing a waveform comparison technique on a frequency axis according to an embodiment of the present invention.

Therefore, with the present example, comparison between a measured waveform and an estimated waveform is performed on the frequency axis. FIG. 11 illustrates a conceptual diagram thereof, and FIG. 3B illustrates degree of coincidence evaluating procedures, respectively. In step S304, the processing unit sets a frequency range or region to be compared. Next, in step S305, the processing unit calculates difference $\delta(\nu)$ between the measured waveform spectrum $E_{meas}(t)$ and the estimated waveform spectrum $E_{est}(t)$. Finally, in step S306, the processing unit calculates the degree of coincidence of both frequency spectra, and stores in the evaluation function $\Delta$. Here, subscripts i and j are numbers corresponding to the material and constitution of each layer to be estimated, and N is the number of data in the evaluation range of the difference $\delta(\nu)$.

$$\Delta(i_1,i_2,\ldots,j_1,j_2,\ldots)=\Sigma|\delta(\nu)|^2/N \quad \text{(Expression 16)}$$

Subsequent steps are the same as with the related art. Here, in the event that material groups A, B, C, . . . , and so on in the evaluation range (candidates) have a characteristic spectrum (absorption line), it is desirable that the agree of coincidence evaluation range is restricted to neighborhood thereof. For example, when materials have an absorption line such that a material A has frequencies $\nu_1$ and $\nu_2$, and a material B has $\nu_3$, and a suitable interval is taken as $\Delta\nu$, the integration range in Expression 16 is set as follows.

$$\nu \in \bigcup_{j=1}^{\infty} |\nu-\nu_j| \leq \Delta\nu \quad \text{(Expression 17)}$$

As described above, discrimination on which material features have been reflected may be made by performing coincidence evaluation on the frequency axis. Also, with the examples described above, it has been estimated that at the time of checking the degree of coincidence between the measured waveform and the estimated waveform, the ranges of parameters such as complex refractivity indexes (refractive index and extinction coefficient) and thickness regarding each layer are determined, and the parameters are changed within the ranges thereof. However, in the event that the parameters are changed in all possible arrangements, even regions which are far off have to be checked, which is inefficient.

On the other hand, with regard to evaluation functions represented in Expressions 10 and 16, a problem in that multiple parameters that minimize their values have to be searched is neither more nor less than a so-called optimization problem. Therefore, parameters taking the minimum value can be searched using an existing optimization technique such as the Newton method, conjugated gradient method, simplex method, or the like. Initial values to be used are provided to the database as references, but their ranges do not have to be specified.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-257595 filed Nov. 26, 2012 and No. 2013-196074 filed Sep. 20, 2013, which are hereby incorporated by reference herein in their entirety.

What is claimed is:

1. A measuring apparatus configured to identify a material and thickness of each of a plurality of layers included in a layered body, based on a measurement result obtained by measuring a time domain waveform of an electromagnetic wave pulse from the layered body, comprising:
a database configured to store data of a plurality of material candidates and a plurality of thickness candidates;
an input unit configured to input a search range of the data of the plurality of material candidates and the plurality of thickness candidates stored in the database; and
a processing unit configured to reproduce a time domain waveform of an electromagnetic wave pulse from the layered body by employing data of a plurality of material candidates and a plurality of thickness candidates within the search range, and to compare this reproduced time domain waveform and the time domain waveform of the measurement result, thereby identifying the material and thickness of each of the plurality of layers.

2. The measuring apparatus according to claim 1, wherein the data of the plurality of material candidates includes a property as to the electromagnetic waves of the plurality of material candidates.

3. The measuring apparatus according to claim 2, wherein the data of the plurality of material candidates includes complex refractive index spectra of the plurality of material candidates.

4. The measuring apparatus according to claim 1, wherein the data of the plurality of material candidates stored in the database has been compressed using wavelets.

5. The measuring apparatus according to claim 1, wherein the processing unit identifies the material and thickness of each of the plurality of layers by comparing the reproduced time domain waveform and the time domain waveform of the measurement result for each point-in-time.

6. The measuring apparatus according to claim 5, wherein an electromagnetic wave pulse from the layered body is an electromagnetic wave pulse reflected at the layered body;
and wherein the processing unit identifies, in the event that an estimated detection point-in-time of a pulse reflected earliest at a m'th interface from the surface of the layered body is taken as tm, the material and thickness of each of the plurality of layers by repeating a loop for setting comparison end point-in-time for each point-in-time to tm, and identifying at least the material of (m+1)'th layer and at least the thickness of a m'th layer of the layered object, while increasing the value of m, thereby identifying the material and thicknesses of each of the plurality of layers.

7. The measuring apparatus according claim 6, wherein the processing unit sets comparison start point-in-time for each point-in-time to less than $tm-\Delta\tau0$;
and wherein, with full width at half maximum of a peak of a time domain waveform of an electromagnetic wave pulse to be irradiated on the layered body as W, a condition of $3W \leq \Delta\tau0 \leq tm$ is satisfied.

8. The measuring apparatus according to claim 1, wherein the processing unit identifies the material and thickness of each of the plurality of layers by comparing a spectrum obtained by subjecting the reproduced time domain waveform to Fourier transformation, and a spectrum obtained by subjecting the time domain waveform of the measurement result to Fourier transformation for each frequency.

9. The measuring apparatus according to claim 1, wherein an electromagnetic wave pulse from the layered body is an electromagnetic wave pulse transmitted from the layered body or electromagnetic wave pulse reflected at the layered body.

10. The measuring apparatus according to claim 1, further comprising:
an irradiation unit configured to irradiate electromagnetic wave pules on the layered body; and
a detecting unit configured to detect electromagnetic waves from the layered body.

11. The measuring apparatus according to claim 10, wherein the layered body is in contact with a plate material which transmits an electromagnetic wave pulse and also of which the complex refractive index and thickness are known;
and wherein the irradiation unit irradiates the electromagnetic wave pulse on the layered body via the plate material, and identifies the material and thickness of each of the plurality of layers using an electromagnetic wave pulse reflected from the plate material and an electromagnetic wave pulse reflected at the layered body.

12. The measuring apparatus according to claim 1, wherein the layered body includes living body tissue.

13. A measuring method to identify a material and thickness of each of a plurality of layers included in a layered body, based on a measurement result obtained by measuring a time domain waveform of an electromagnetic wave pulse from the layered body, the method comprising:
obtaining a search range of data of a plurality of material candidates and a plurality of thickness candidates stored in a database;
reproducing a time domain waveform of an electromagnetic wave pulse from the layered body by employing data of a plurality of material candidates and a plurality of thickness candidates within the search range; and
identifying the material and thickness of each of the plurality of layers by comparing the reproduced time domain waveform and the time domain waveform of the measurement result.

14. A program stored in a non-transitory computer-readable storage medium, the program causing a computer to execute the processes of the measuring method according to claim 13.

* * * * *